United States Patent [19]

Umemura et al.

[11] Patent Number: 5,435,311
[45] Date of Patent: Jul. 25, 1995

[54] ULTRASOUND THERAPEUTIC SYSTEM

[75] Inventors: Shinichiro Umemura, Hachioji; Kenichi Kawabata, Saitama; Koji Kawaguchi, Kokubunji; Hiroshi Ikeda, Hachioji, all of Japan

[73] Assignee: Hitachi, Ltd., Tokyo, Japan

[21] Appl. No.: 243,321

[22] Filed: May 16, 1994

Related U.S. Application Data

[63] Continuation of Ser. No. 843,595, Feb. 28, 1992, abandoned, which is a continuation-in-part of Ser. No. 373,264, Jun. 27, 1989, Pat. No. 5,158,071.

[30] Foreign Application Priority Data

Feb. 28, 1991 [JP] Japan ............................ 3-034008
May 16, 1991 [JP] Japan ............................ 3-111455

[51] Int. Cl.⁶ .......................................... A61B 17/22
[52] U.S. Cl. .................................. 128/660.03; 601/3; 601/4; 607/97
[58] Field of Search ............... 128/660.03; 601/2-4; 607/97

[56] References Cited

U.S. PATENT DOCUMENTS

| | | |
|---|---|---|
| 4,483,345 | 11/1984 | Miwa . |
| 4,620,546 | 11/1986 | Aida . |
| 4,658,828 | 4/1987 | Dory . |
| 4,844,079 | 7/1989 | Naser et al. . |
| 4,865,042 | 9/1989 | Umemura et al. . |
| 5,005,579 | 4/1991 | Wurster et al. . |
| 5,150,713 | 9/1992 | Okazaki . |
| 5,158,085 | 10/1982 | Belikan et al. . |
| 5,174,294 | 12/1992 | Saito et al. . |

FOREIGN PATENT DOCUMENTS 3704909  8/1988  Germany .

*Primary Examiner*—Ruth S. Smith
*Attorney, Agent, or Firm*—Antonelli, Terry, Stout & Kraus

[57] ABSTRACT

In an ultrasound therapeutic system provided with an ultrasound transmitter having a focusing mechanism and a plurality of groups of ultrasound transmitters/receivers, each of which has a controllable directivity, each of the transmitters/receivers is constructed so as to be able to receive both echo of pulse-shaped ultrasound transmitted by itself and even order harmonic signals of the ultrasound transmitted by the transmitter, and a plurality of two-dimensional pulse echographical images constructed by ultrasound signals obtained by transmitting/receiving beams, while controlling the directivity of the beam emitted by each of the plurality of groups of ultrasound transmitters/receivers and a plurality of images indicating orientation and intensity, in which an even order harmonic wave signal due to the ultrasound transmitted by the transmitter is received by each of the plurality of groups of ultrasound transmitters/receivers, are displayed, superimposed on each other.

3 Claims, 5 Drawing Sheets

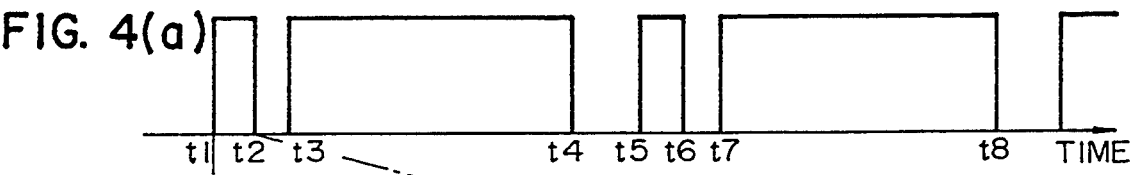
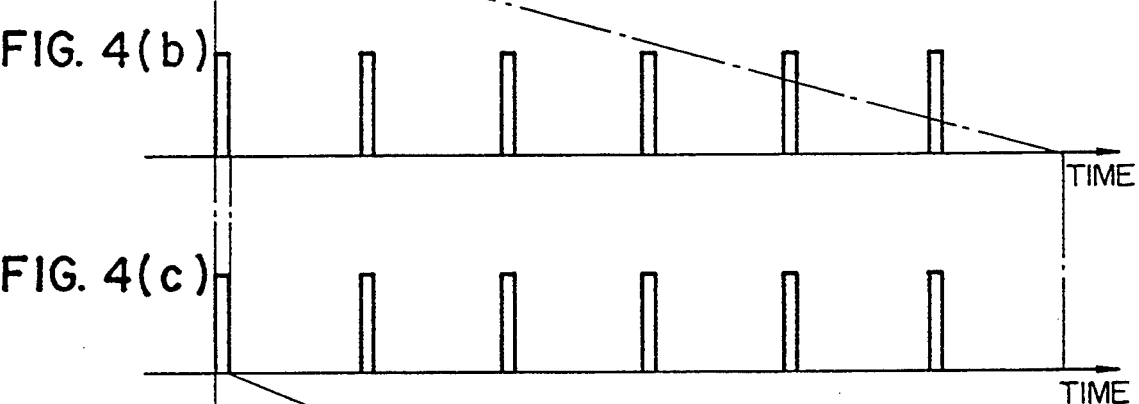
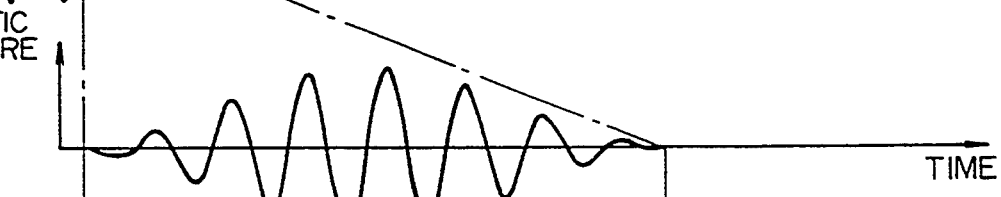
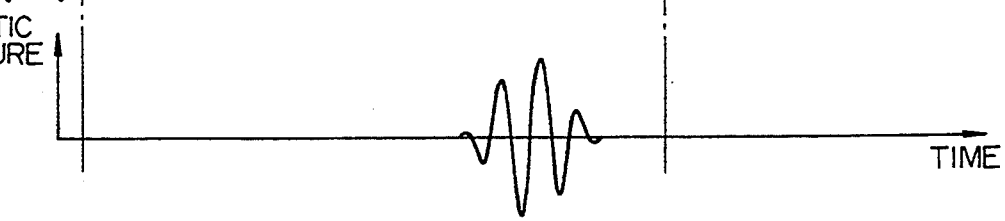

ULTRASOUND THERAPEUTIC SYSTEM

This application is a Continuation of application Ser. No. 07/843,595, filed Feb. 28, 1992 now abandoned, which is a continuation-in-part of U.S. application Ser. No. 07/373,264, filed Jun. 27, 1989 U.S. Pat. No. 5,158,071 which is incorporated by reference.

BACKGROUND OF THE INVENTION

The present invention relates to an ultrasound therapeutic system suitable for therapy for malignant tumors, therapy for calculi, etc. It has been proposed by U.S. Pat. No. 4,821,730 to add aiming and monitoring function by ultrasound to a lithotriptor with ultrasound or shockwave, which makes more suitable treatment possible. According to this U.S. Patent, an ultrasonic probe, which is relatively small with respect to a transmission aperture for ultrasound or shockwave, is integrated therein to effect aiming and monitoring by ultrasound. Since acoustic wave is used both for producing therapeutic effects and for aiming and monitoring, this system has advantages in principle that it has a self-matching property and that it is possible to suppress aiming errors due to influences of refraction, etc. in a living body to a low level.

SUMMARY OF THE INVENTION

The technique described above has made therapy by focused ultrasound wave with small aiming errors possible. However, in the case where it is considered from the view point of the aiming and the monitoring, one cannot help but say that only the technique described above is insufficient. That is, in the case of lithotomic therapy, since it is possible to judge whether shockwave hits a calculus or not by monitoring on an ultrasound image that the calculus subjected to the shockwave is moved by radiation force, it is possible to judge whether a target position is correctly irradiated or not. However, in the case of therapy for malignant tumors, since differences in acoustic impedance between the tumors and surrounding tissue are slight, it is difficult to monitor on the ultrasound image movements of a part to be treated by radiation force.

In addition, in the case of therapy for malignant tumors, the therapy is effected by producing cavitations at the part to be treated by the shockwave. However, from the view point of preventing side effect on the surrounding tissue, it is important to monitor and suppress the cavitations produced at parts other than the target part to be treated. This is extremely difficult only by the technique described above, because differences in acoustic impedance among the target part to be treated, the surrounding tissue and the cavitations are slight.

The object of the present invention is to solve such a problem and to realize a system capable of monitoring precisely that focused ultrasound for therapy hits the target part to be treated. In this way therapy by focused ultrasound producing scarcely side effect at parts other than the target part to be treated can be realized.

In order to achieve the above object according to the present invention, a monitoring ultrasound transmitter/receiver having a directivity, by which scanning is possible, is added for aiming and monitoring to a focused ultrasound generating transmitter, as described in the U.S. Pat. No. 4,821,730 described above. The monitoring ultrasound transmitter/receiver is so constructed that not only it receives echo of pulsed ultrasound transmitted by itself, but also it can receive even order harmonic wave signals, which ultrasound transmitted by the focused ultrasound generating transmitter produces at the part to be treated.

Further, according to the present invention, disposing a plurality of groups of monitoring ultrasound transmitters/receivers at different positions, it is possible to monitor continuously a plurality of two dimensional pulse echo images by receiving echos of the pulsed ultrasound transmitted by themselves, and a plurality of images representing orientation and intensity in which even order harmonic wave signals, which ultrasounds transmitted by the focused ultrasound generating transmitter described above produce at the part to be treated, are received by the plurality of groups of monitoring ultrasound transmitters/receivers, by constructing the system so as to display them superimposed on each other.

In addition, according to the present invention, disposing only one monitoring ultrasound transmitter/receiver, sampling-like monitoring utilizing interruption is possible by constructing the system so as to display a pulse echo image obtained by receiving echos of the pulsed ultrasound transmitted by itself, and an image representing orientation and intensity, in which interruptions of even order harmonic wave signals produced at the part to be treated, by interrupting generation of the focused ultrasound in the focused ultrasound generating transmitter, superimposed on each other.

For example, as described in Ser. No. 07/373,264 (filed Jun. 27, 1989), which is the parent application now U.S. Pat. No. 5,158,071 of the present application, sounds of even order harmonics of the focused ultrasound are produced, in many cases, from the region where calculi are destructed or from the region where destruction of tumor tissue accompanied by collapse of cavitations takes place. According to the invention of the present application these even order harmonics are received by the focused ultrasound generating transmitter to be utilized. That is, not only aiming, but also continuous or sampling-like monitoring of the irradiated position during irradiation with ultrasound can be effected owing to imaging by means of the monitoring ultrasound transmitter/receiver having a directivity, by which scanning is possible, and to imaging by receiving even order harmonics produced by irradiation with the focused ultrasound by means of the focused ultrasound generating transmitter.

BRIEF DESCRIPTION OF THE DRAWING

FIG. 4(a)-4(f) are waveform diagrams representing timing relation at focused ultrasound transmission in the second embodiment of the present invention.

DESCRIPTION OF THE PREFERRED EMBODIMENTS

Hereinbelow the present invention will be explained, referring to two embodiments.

Figure 1:
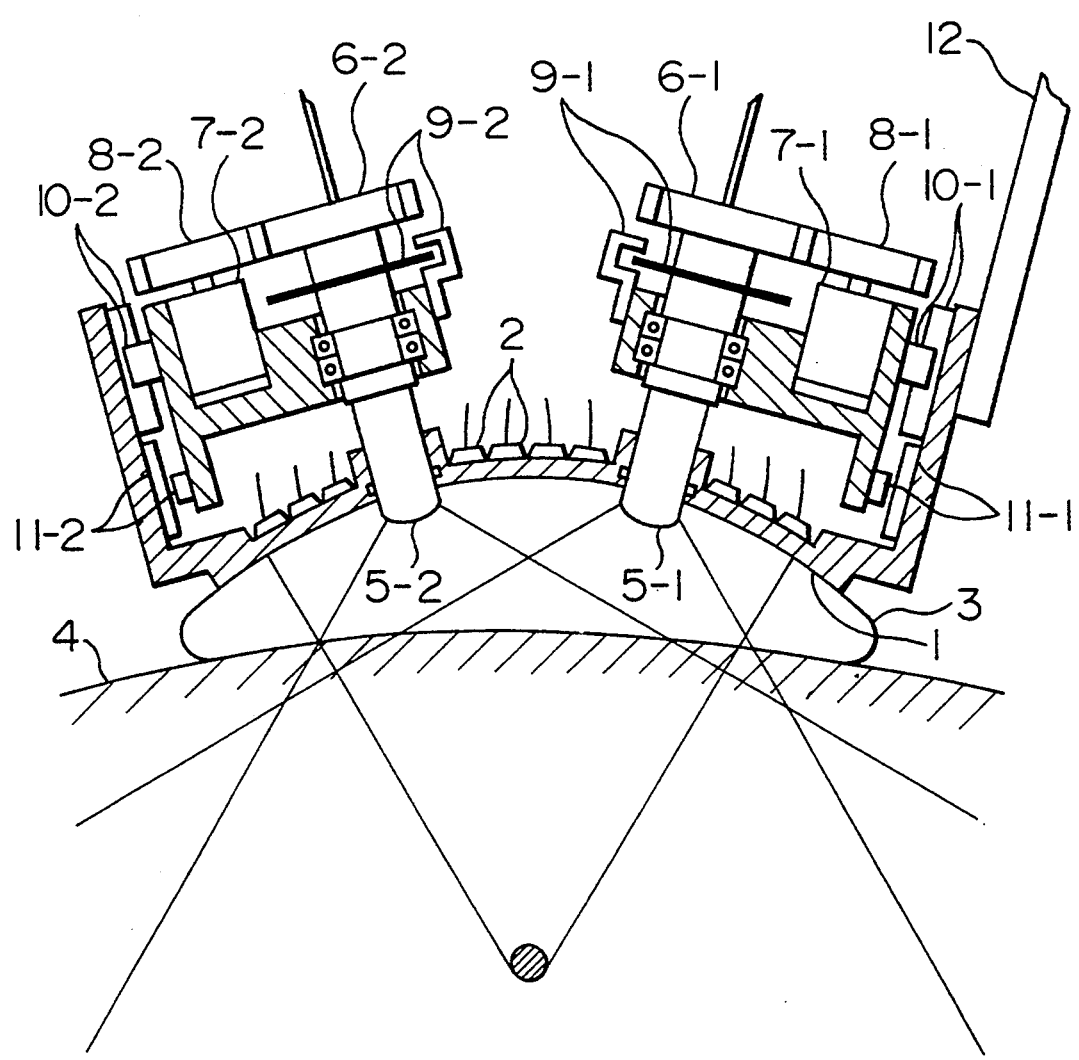
FIG. 1 is a cross-sectional view of an applicator, which is an embodiment of the present invention.
Figure 2:
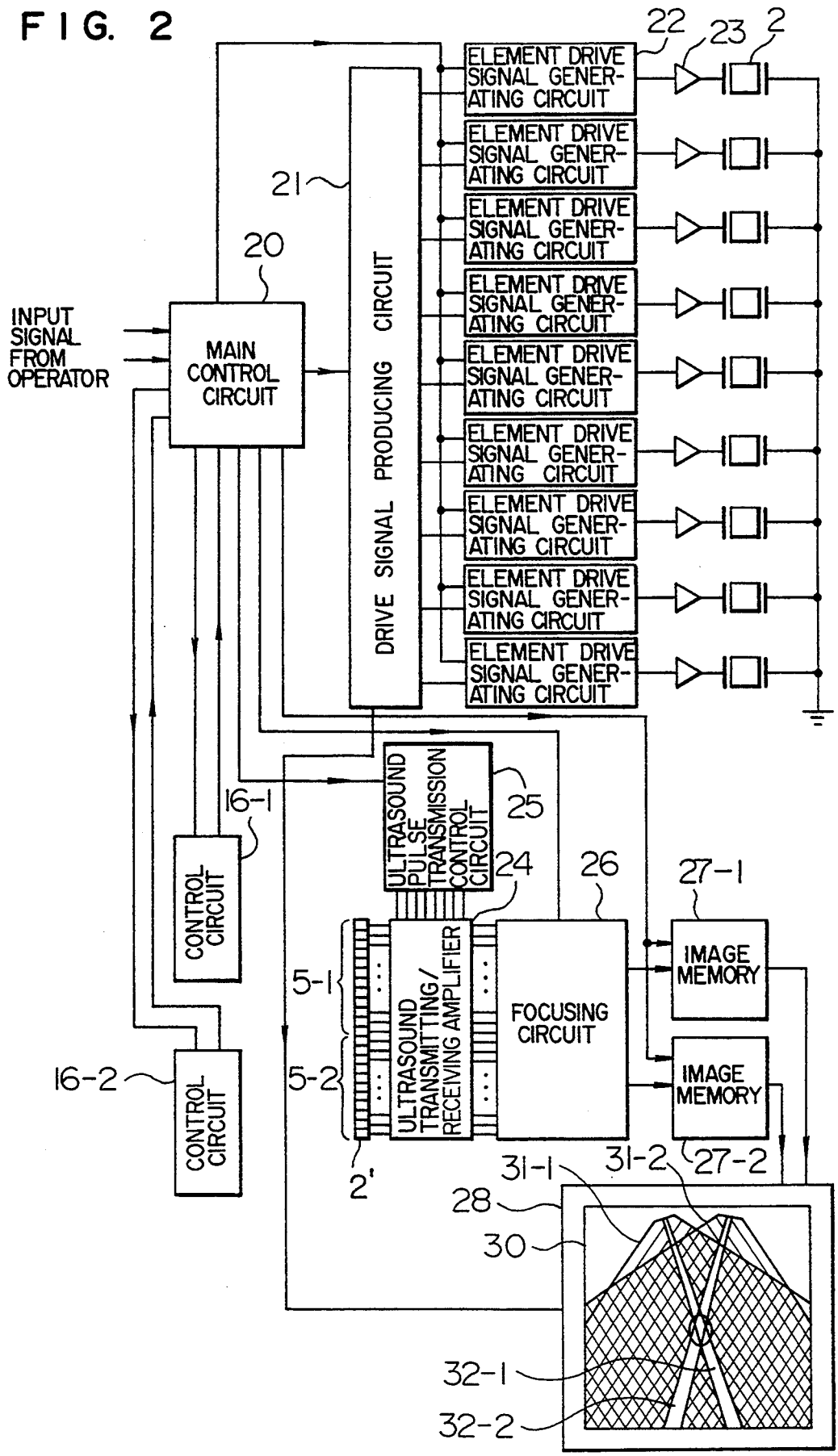
FIG. 2 is a diagram showing the circuit construction of a whole therapeutic system representing a first embodiment of the present invention.

FIGS. 1 and 2 are a cross-sectional view of an applicator and a diagram showing the circuit construction of a whole therapeutic system representing a first embodiment of the present invention.

A focused ultrasound generating transmitter used for the applicator consists of a base plate 1 made of light metal serving as an acoustic matching material, a ground electrode and a heat sink in common, to one surface of which a number of piezoelectric elements 2 made of piezoelectric ceramics (these are so selected that the resonance frequency is 750 kHz) are adhered. Further, on the other surface of the light metal base plate 1, a water bag 3 filled with degassed water is mounted as an acoustical coupler for the body 4 of a patient to be treated. A concave spherical curvature is given to the light metal base plate 1 in order to make it possible to focus acoustic wave on an affected part to be treated and to move the focal point within a region to be treated by using a necessary number of transducer elements as small as possible.

On the applicator two monitoring ultrasound transmitters/receivers 5-1 and 5-2 are mounted, in order to make aiming with focused ultrasound on the affected part to be treated and continuous monitoring during irradiation with the focused ultrasound by means of an ultrasound image possible. Each of the monitoring ultrasound transmitters/receivers is composed of an array-shaped ultrasound transducer consisting of e.g. 100 piezoelectric elements 2', by means of which ultrasonic imaging by the electronic scanning pulse echographic method is possible. Toothed wheels 6-1 and 6-2 are mounted over the monitoring ultrasound transmitters/receivers 5-1 and 5-2, respectively, and they are so constructed that they can be rotated through toothed wheels 8-1 and 8-2 mounted on the extremities of rotating motors 7-1 and 7-2, respectively. The rotational angles thereof are detected by rotary encoders 9-1 and 9-2, respectively. Linear motors 10-1 and 10-2 are mounted on the whole monitoring ultrasound transmitters/receivers 5-1 and 5-2, respectively, so that they can be moved up- and down-wards. Amounts of the up and down displacement thereof are detected by linear encoders 11-1 and 11-2, respectively. The whole applicator is mounted on a holding mechanism (not shown in the figure) disposed outside through an arm 12.

The applicator described above, which is the first embodiment of the present invention, is controlled by a circuit of the whole therapeutic system indicated in FIG. 2, as described below.

The rotation and the translation of the monitoring ultrasound transmitters/receivers 5-1 and 5-2 are effected by driving the rotating motors 7-1 and 7-2 and the linear motors 10-1 and 10-2 by means of control circuits 16-1 and 16-2 connected to a main control circuit 20 through operating signals, which an operator gives to the main control circuit 20. The rotational angles and the amounts of up- and down-ward displacement are detected and fed back to the main control circuit 20.

Monitoring ultrasound is emitted by the monitoring ultrasound transmitters/receivers 5-1 and 5-2 controlled by an ultrasound pulse transmission control circuit 25 triggered by the main control circuit 20 through an ultrasound transmission/reception amplifier 24. Reflected waves of the transmitted monitoring ultrasound are received by the monitoring ultrasound transmitters/receivers 5-1 and 5-2 and converted into imaged ultrasound pulse echographic images by a received wave beam scanning and focus circuit 26 triggered by the main control circuit 20 through the ultrasound transmission/reception amplifier 24. The ultrasound pulse echographic images by the monitoring ultrasound transmitters/receivers 5-1 and 5-2 are once recorded in image memories 27-1 and 27-2 and displayed on a displaying screen of a display device 28 as two-dimensional tomographic images 31-1 and 31-2, respectively, as indicated by hatching lines having different directions, superimposed on each other, as shown in the figure. Since transmission/reception of the monitoring ultrasound, conversion itself thereof into the ultrasound pulse echographic images and display thereof on the displaying device are well-known, explanation thereof will be omitted.

Further, when the monitoring ultrasound transmitters/receivers 5-1 and 5-2 are rotated, while transmitting the monitoring ultrasounds, it is possible to form three-dimensional images within conical regions determined by respective directive beam scanning angles. In a region where these two conical regions are superposed on each other, a three-dimensional image doubly superimposed is obtained.

In the case where therapy using this applicator is effected, a doctor moves the applicator up to a position suitable for therapy for an affected part, while observing the displayed image, and fixes it there. Thereafter he gives necessary operation signals thereto through the main control circuit 20, aims at the affected part with the focal point of the focused ultrasounds, and transmits the focused ultrasounds on a trial or experimental basic by means of a drive signal producing circuit 21, an element drive signal generating circuit 22 and a drive amplifier 23. At this time, in the neighborhood of the focal point of the focused ultrasound harmonics and in particular even order harmonics are produced by nonlinear effects. This harmonic signal passes through the same path and it is subjected to the same processing as the ultrasonic pulse echo signal. Then it is displayed, superimposed on the pulse echographic image. That is, it is received by the transmitters/receivers 5-1 and 52, passes through the ultrasound transmission/reception amplifier 24 and the received wave beam scanning and focus circuit 26, is recorded once in the image memories 27-1 and 27-2, and is displayed on the display screen 30 as linear line band-shaped images 32-1 and 32-2, respectively, superimposed on each other. It is because transmission of the focused ultrasounds is effected not in a pulsed shape but continuously and generation of harmonics by them is also continuous that they are displayed as liner band-shaped images. By an imaging system using a single monitoring ultrasound transmitter/receiver it is impossible to detect the position in the depth direction of the generation of the harmonics. On the contrary, in the first embodiment, since it is provided with an imaging system using two monitoring ultrasound transmitters/receivers, the generation point of the harmonics, i.e. the focal point of the focused ultrasounds, is displayed and detected as a position, where the two band-shaped images 32-1 and 32-2 intersect each other in the two-dimensional tomographic image.

The doctor, who effects the therapy by means of this system, carries out the main irradiation with the focused ultrasound, after having confirmed that the position, where harmonics are generated, is in accordance with the affected part. In the case where the position, where harmonics are generated, is deviated from the affected part, the operation signal given through the main control circuit 20 is corrected and the irradiation is carried out again, after having corrected the focal point of the focused ultrasound in an electronic manner by means of the drive signal circuit 21.

Further, in the case where it is judged that the degree of the generation of the harmonics is not appropriate, too small or too great, the magnitude of the output of the drive signal producing circuit 21 acting as the focused ultrasound intensity signal is displayed on the display screen 30 and the irradiation is carried out again, after having corrected the operation signal, referring thereto.

Since the focal point of the focused ultrasound thus obtained is displayed continuously during the transmission of the focused ultrasound, the doctor can take a measure to interrupt the transmission of the focused ultrasound as soon as the focal point of the focused ultrasound is deviated or becomes otherwise inappropriate, which makes a safer therapy possible.

Here, although it is well known how to determine the focal point of the focused ultrasound, it will be briefly explained.

That is, denoting the center of each of the piezoelectric elements constituting the array type focused ultrasound generator by Pn (n=1, ---, N) (here N being e.g. 100), the target focal point by F; the length of a segment $\overline{PnF}$ by dn; an approximate value of the sound velocity in a living body by c; and the frequency of the focused ultrasound by f, the ultrasound can be focused at the target focal point F by driving the different piezoelectric elements by using a drive signal having a phase $\phi n$ given by a following equation at a point of time t:

$$\phi n = 2\pi f \left( t - \frac{dn}{c} \right).$$

Here the difference between the sound velocity in the water bag and the sound speed in the living body as well as the sound speed distribution in the living body are neglected. A part or a major part of deviations of the focal point F due to the refractive effect of sonic wave produced by the fact that these are not zero can be corrected selfconsistently by effecting determination of the phase at the transmission and the reception of the monitoring ultrasound in the same way as described above. That is, there is essentially no problem, because errors are produced in a similar manner for the irradiation for therapy and for the transmission and the reception for monitoring.

Calculations for the drive phase $\phi n$ as described above are carried out in the drive signal producing circuit 21. A result thus obtained is sent to the element drive signal generating circuit 22 and the different piezoelectric elements are driven by the drive amplifier 23. The electronic focal point scanning with the focused ultrasound is realized in this way. Consequently, when it is desired to vary the depth of the focal point, it is sufficient e.g. to give operation signals for varying dn in the above equation.

In the present embodiment the system was so constructed that the two transmitters/receivers were disposed inside of the water bag. This is a construction efficient for detecting cavitations produced inside of the water bag at the same time. However, in the case where it is aimed to detect exclusively cavitations produced within the body of the patient to be treated, it is desirable to adopt a construction, in which the transmitters/receivers are placed outside of the water bag. Further, in this case, there may be another method, by which any water bag, which is apt to be a cavitation generating source, is not used at all.

Furthermore, in order to display an image obtained by a plurality of ultrasound transmitters/receivers 5 so as to be more easily observed, it is preferable to use a color display and to make different color tones correspond to the image signals from the different ultrasound transmitters/receivers.

Next the second embodiment of the present invention will be explained. The applicator in this embodiment includes only one imaging system using a monitoring ultrasound transmitter/receiver. An example of the construction is essentially identical to that indicated in FIG. 1 and it is omitted to show it in the figure. That is, between the monitoring ultrasound transmitters/receivers 5-1 and 5-2 in the applicator indicated in FIG. 1 the parts relating to that indicated by 5-2 are removed and that indicated by 5-1 is located at the central portion of the focused ultrasound generating transmitter in the applicator. Also in the present embodiment, the focused ultrasound generating transmitter consists similarly of a base plate 1 made of light metal serving as an acoustic matching material, a ground electrode and a heat sink in common, to one surface of which a number of piezoelectric elements 2 made of piezoelectric ceramics (these are so selected that the resonance frequency is 750 kHz) are adhered.

Figure 3:
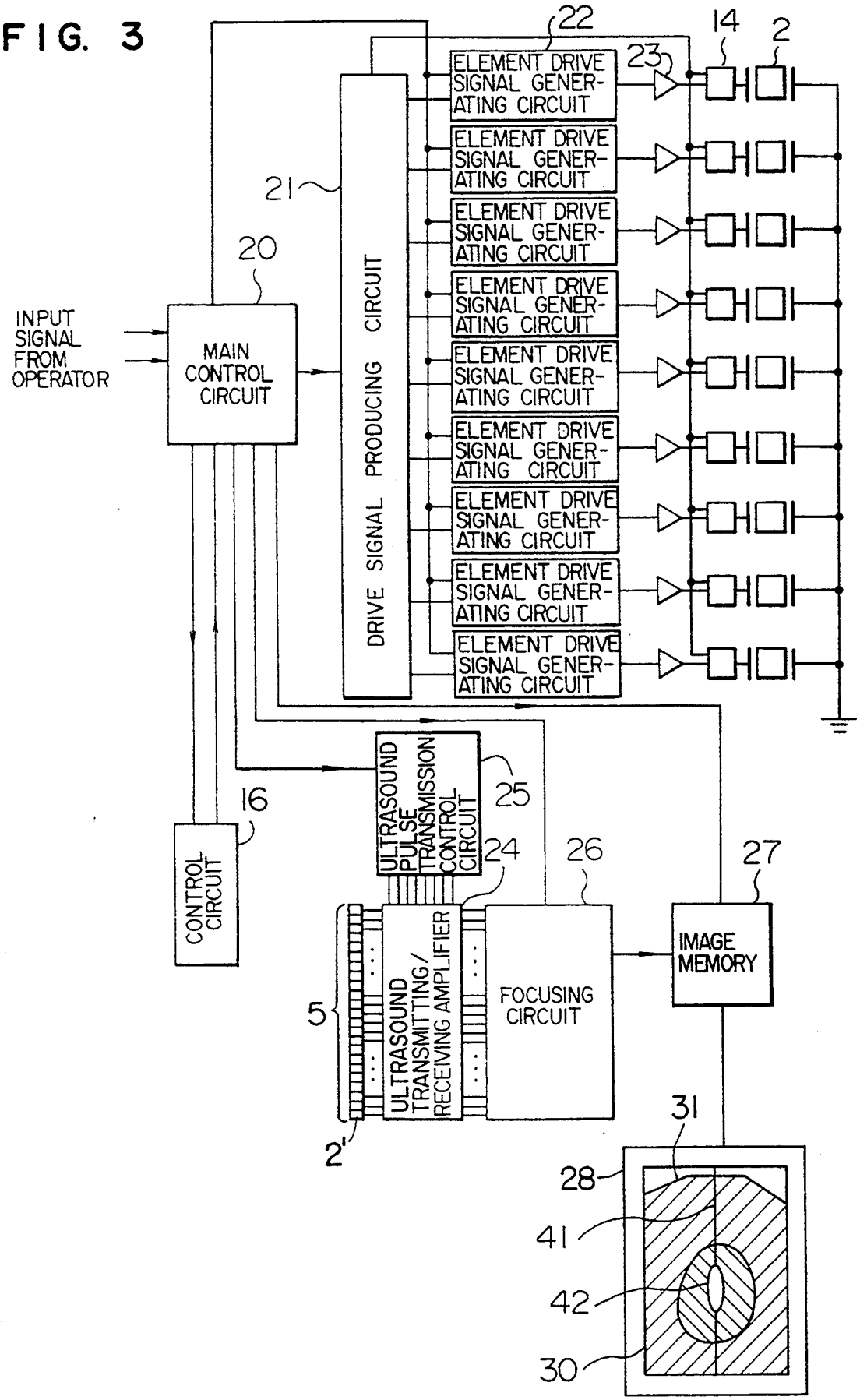
FIG. 3 is a block diagram showing the circuit construction of a whole therapeutic system representing a second embodiment of the present invention.

FIG. 3 is a block diagram showing the circuit construction of a whole therapeutic system representing a second embodiment. In FIG. 3, the parts having same functions as those shown in FIG. 2 are indicated by the same reference numerals. As clearly seen by comparing the two, in the second embodiment there is only one imaging system by the monitoring ultrasound transmitter/receiver. Therefore the imaging system consisting of the ultrasound pulse transmission control circuit 25 triggered by the main control circuit 20; the monitoring ultrasound transmitter/receiver 5 transmitting monitoring ultrasound through the ultrasound transmission/reception amplifier 24 by means thereof; the received wave beam scanning and focus circuit 26, which receives reflected waves of the transmitted monitoring ultrasound by means of the monitoring ultrasound transmitter/receiver 5, and converts them into an ultrasound pulse echographic image, triggered by the ultrasound transmission/reception amplifier 24 and the main control circuit 20, can be simplified. Similarly to the first embodiment, an image obtained by receiving reflected waves of the monitoring ultrasound is displayed on the screen 30 of the display device 28, as indicated by the hatching 31.

On the other hand, necessary operation signals are given through the main control circuit 20 to aim at the affected part with the focal point of the focused ultrasound and a variable resonance circuit 14 is added to the focused ultrasound irradiation system consisting of piezoelectric elements 2 emitting focused ultrasound, triggered by the drive signal producing circuit 21, the element drive signal generating circuit 22 and the drive amplifier 23. As described later, these are disposed for transmitting the focused ultrasound in a pulsed shape; receiving even order harmonics generated in the neighborhood of the focal point of the focused ultrasound by the monitoring ultrasound transmitter/receiver 5; displaying an image thus obtained, superimposed on the pulse echographic image; and detecting the position of the focal point in the depth direction.

FIG. 4 is a diagram indicating waveform and timing at the focused ultrasound transmission in the second embodiment.

As indicated in the timing chart shown by (a) in the figure, imaging and aiming by the pulse-shaped ultrasound are effected during a period of time from a point of time t1 to another point of time t2. Thereafter the focused ultrasound is transmitted continuously from a point of time t3 to another point of time t4. Then, thereafter, imaging and aiming by the pulse-shaped ultrasound are effected again from a point of time t5 to another point of time t6. Then, thereafter, continuous transmission of the focused ultrasound is started again at a point of time t7. Subsequently the same process is repeated for a required irradiation period of time.

That is, before the continuous transmission of the focused ultrasound, the focal point of the focused ultrasound in the depth direction is confirmed in the two-dimensional tomographic image by transmitting and receiving the pulse-shaped focused ultrasound. When the focal point is inappropriate, the focal point of the focused ultrasound is confirmed again by transmitting and receiving the pulse-shaped focused ultrasound after having given operation signals for adjusting the focal point to recalculate the drive phase by means of the drive signal producing circuit 21 in order to correct the focal point. After the start of the continuous transmission, the continuous transmission is once interrupted after having been continued the continuous transmission for a predetermined period of time, in order to confirm the focal point of the focused ultrasound by transmitting and receiving the pulse-shaped focused ultrasound. When it is confirmed at thus stage that the focal point is inappropriate, similarly to the start of the transmission, the focal point of the focused ultrasound is confirmed again by transmitting and receiving the pulse-shaped focused ultrasound, after having given operation signals for adjusting the focal point to correct it.

The imaging by transmitting and receiving the pulse-shaped ultrasound as described above is performed, based on a principle basically identical to the imaging principle of the pulse echo method widely used for ultrasound therapeutic systems. However, it is characterized in that the system is so constructed that the pulse-shaped ultrasound is transmitted also from the focused ultrasound generator in synchronism with the transmission of the pulse-shaped ultrasound similar to that transmitted by an ultrasound therapeutic system where it is transmitted from the monitoring ultrasound transmitter/receiver 5, in order to make the aiming with the focused ultrasound possible.

This aspect will be explained in detail, referring to FIGS. 4(a)–4(f). The timing charts indicated by FIGS. 4(d)–(f) represent transmission timing of the pulse-shaped ultrasound from the focused ultrasound generator and the monitoring ultrasound transmitter/receiver, respectively, and 4(d) and 4(f) represent transmission waveforms (acoustic pressures) in respective timing enlarged in the time scale. Since the transmitting fronts of the focused ultrasound generator and the monitoring ultrasound transmitter/receiver are, in general, not coplanar, as indicated in FIG. 1, the pulse-shaped ultrasound transmitted by the focused ultrasound generator passes through the position corresponding to the transmitting front of the monitoring ultrasound transmitter/receiver with a predetermined delay time td, as indicated by FIG. 4(e). Since this delay td can be determined, based on the construction of the system, the imaging pulse-shaped ultrasound of relatively high frequency is transmitted by the monitoring ultrasound transmitter/receiver, taking this timing into account, as indicated by FIG.(f). Here, as clearly seen from comparing 4(e) and 4(f), it is desirable that the acoustic pressures of the pulse-shaped ultrasound transmitted by the focused ultrasound generator and the imaging pulse-shaped ultrasound transmitted by the monitoring ultrasound transmitter/receiver are greatest with a same timing.

In the case where the transmission/reception direction of the imaging pulse-shaped ultrasound is in accordance with the direction of the focal point of the focused ultrasound, the transmitted pulse-shaped focused ultrasound and the imaging pulse-shaped ultrasound arrive almost simultaneously at the neighborhood of the focal point of the focused acoustic wave and a part of energy of the pulse-shaped ultrasound, which has been focused to have a high intensity, is converted into harmonics in the same frequency band as the imaging ultrasound by a non-linear phenomenon. These harmonics have the highest intensity in the proximity of the focal point of the focused ultrasound and they are scattered by scatterers in the neighborhood of the focal point of the focused ultrasound approximately at the same time as the imaging pulse-shaped ultrasound. Scattered ultrasounds are received further similarly almost simultaneously by the monitoring ultrasound transmitter/receiver 5 and inputted to the received wave beam scanning and focus circuit 26, where they are treated similarly to the imaging pulse echo signal. Consequently a received signal is obtained, in which a signal due to the harmonics of the pulse-shaped focused ultrasound is superimposed on the usual imaging pulse echo signal due to the transmission/reception by the monitoring ultrasound transmitter/receiver at the position corresponding to the focal length of the focused ultrasound.

In this way, an image indicating the position, where the harmonics are generated by the focused ultrasound, is obtained in a state, where it is superimposed on the pulse echographic image 31, as indicated in FIG. 3. A line 41 in FIG. 3 indicates the position of the rotational axis of the monitoring ultrasound transmitter/receiver 5. Since it can be easily realized by giving a signal corresponding to the position thereof to construct it on an imaging screen, it is not specifically explained.

Now, when the scanning plane by the transmission/reception of the imaging pulse-shaped ultrasound doesn't include the position, where the harmonics are generated by the focused ultrasound, the harmonics of the pulse-shaped focused ultrasound generated in the neighborhood of the focal point of the focused ultrasound don't appear on the imaging screen. At this time, the operator may vary the position of the rotational axis of the monitoring ultrasound transmitter/receiver or rotate the last so that the harmonics of the pulse-shaped focused ultrasound appear on the imaging screen, to know the correct position of the irradiation.

Further the image accompanied by the generation of the harmonics by the focused ultrasound is in a band-shaped, as indicated by 32-1 or 32-2 in FIG. 2, during the continuous transmission of the focused ultrasound and it is not possible to know the position, where the harmonics are generated, in the depth direction.

In the present second embodiment, it is possible to know the position, where the harmonics are generated by the focused ultrasound, in the depth direction by making the transmission of the focused ultrasound, which should be transmitted originally continuously, in a pulse shape in a sampling-like manner. For this reason it is necessary to make the transmission of the focused ultrasound by the piezoelectric elements 2 either in a pulse shape or continuous and the device therefor is the addition of the variable resonance circuit 14.

Figure 5:
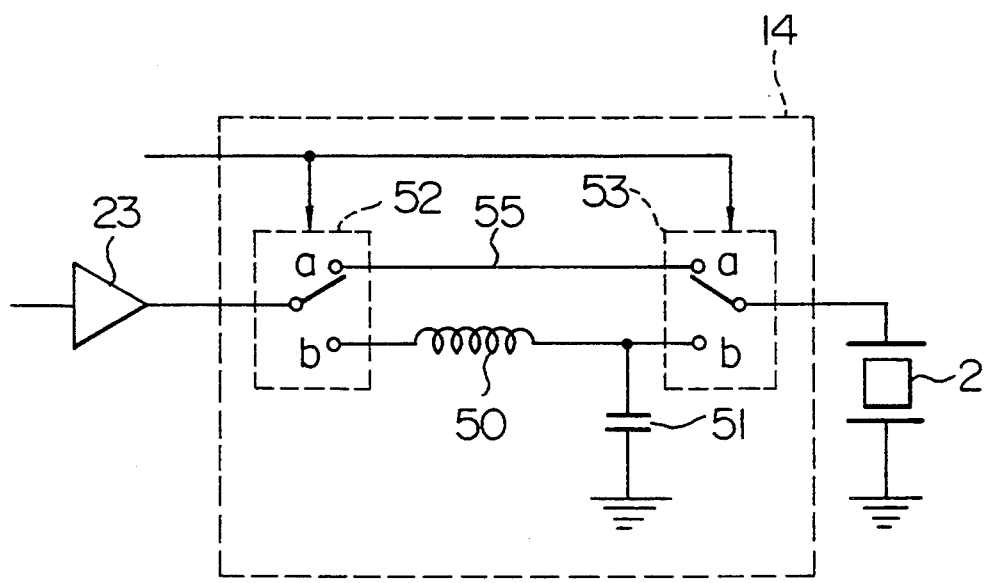
FIG. 5 is a circuit diagram showing an example of a variable resonance circuit used in the second embodiment of the present invention.

FIG. 5 is a partial diagram, in which only the part of the variable resonance circuit 14 is taken out from the circuit construction of the whole therapeutic system shown in FIG. 3 to be indicated. The variable resonance circuit 14 consists of a resonance circuit composed of an inductance 50 and a capacitance 51, a short-circuiting circuit 55 bypassing this resonance circuit, and switches 52 and 53 for selecting them. The switches 52 and 53 are changed over by a signal from the drive signal calculating circuit 21. That is, the switches are connected on the terminal a side at the transmission of the pulse-shaped focused ultrasound for a time period indicated by t1-t2 or t5-t6 to exclude the resonance circuit, attaching importance to pulse characteristics. The switches are connected on the terminal b side at the continuous transmission of the focused ultrasound to include the resonance circuit 50, 51, attaching importance to the efficiency. Consequently the drive of the piezoelectric elements 2 is effected with characteristics suitable for either one of the cases, transmission of the pulsed focused ultrasound and continuous transmission of the focused ultrasound.

As described above, according to the present invention, it is possible to realize a therapeutic system, by which it can be easily confirmed on an image that the focused ultrasound is correctly focused on an affected part and as the result a safer therapy can be made possible.

We claim:

1. An ultrasound therapeutic system comprising:

an ultrasound transmitter having focusing means for continuously transmitting focused ultrasonic waves;

monitoring transmitter/receiver means having a controllable directivity for transmitting monitoring ultrasonic waves and for determining an aiming position for the focused ultrasonic waves, said monitoring transmitter/receiver means including two transmitter/receiver units receiving harmonic wave signals of the continuously transmitted focused ultrasonic waves produced by non-linear effects in the region of the aiming position;

converting means coupled to the monitoring transmitter/receiver means for converting reflected ultrasonic waves to echographical image information; and display means coupled to the converting means for displaying, in superimposed relation, an echographical image based on reflected ultrasonic waves corresponding to the monitoring ultrasonic waves and an echographical image based upon reflected ultrasonic waves corresponding to the focused ultrasonic waves.

2. A system according to claim 1, wherein the converting means includes received wave beam scanning and focusing means for receiving reflected ultrasonic waves of the transmitted monitoring ultrasonic waves and for converting the received reflected ultrasonic waves to echographical image information, and image memories for recording the echographical image information.

3. A system according to claim 1, wherein the ultrasound transmitter includes a plurality of piezoelectric ceramic elements on one surface of a light metal baseplate.

* * * * *